United States Patent
Hahn et al.

(10) Patent No.: US 9,649,207 B2
(45) Date of Patent: May 16, 2017

(54) POWERED PROSTHETIC DEVICES USING EMG-BASED LOCOMOTION STATE CLASSIFIER

(71) Applicant: University of Oregon, Eugene, OR (US)

(72) Inventors: Michael Hahn, Eugene, OR (US); Deepak Joshi, Eugene, OR (US)

(73) Assignee: University of Oregon, Eugene, OR (US)

( * ) Notice: Subject to any disclaimer, the term of this patent is extended or adjusted under 35 U.S.C. 154(b) by 30 days.

(21) Appl. No.: 14/903,009

(22) PCT Filed: Jul. 7, 2014

(86) PCT No.: PCT/US2014/045608
§ 371 (c)(1),
(2) Date: Jan. 5, 2016

(87) PCT Pub. No.: WO2015/006235
PCT Pub. Date: Jan. 15, 2015

(65) Prior Publication Data
US 2016/0158033 A1    Jun. 9, 2016

Related U.S. Application Data

(60) Provisional application No. 61/845,905, filed on Jul. 12, 2013.

(51) Int. Cl.
*A61F 2/72* (2006.01)
*A61F 2/60* (2006.01)
(Continued)

(52) U.S. Cl.
CPC ............ *A61F 2/72* (2013.01); *A61B 5/04888* (2013.01); *A61B 5/1123* (2013.01);
(Continued)

(58) Field of Classification Search
None
See application file for complete search history.

(56) References Cited

U.S. PATENT DOCUMENTS 5,919,149 A   7/1999   Allum
6,093,149 A   7/2000   Guracar
(Continued)

OTHER PUBLICATIONS

Sijiang Du: "Feature Extraction for Classification of Prehensile Electromilgraphy Patterns," Ch. 5, Department of Computer Science, PhD Thesis, SDSU, Dec. 2003.
(Continued)

*Primary Examiner* — David H Willse
(74) *Attorney, Agent, or Firm* — Lumen Patent Firm

(57) ABSTRACT

Real-time control of a prosthetic device using EMG-based locomotion state classification computes a histogram [208] of a time-frequency spectrogram [206] of the EMG data [200] sampled from muscles, classifies the histogram using if-else rules [212] as representing a locomotion steady state [216] or locomotion transition state [214] in the prosthetic device, and controls the prosthetic device using the computed transitions between locomotion modes. The classification may be based on a comparison of feature values [210] derived from the histogram and stored feature values derived from histograms of known locomotion states. Alternatively, the classification may be based on matching scores calculated from the histogram and stored histograms of known locomotion states. The classifying preferably is performed using hierarchical if-else fuzzy classification rules [212], and may further include using a prior locomotion state and a state diagram specifying constraints on locomotion states accessible from other locomotion states.

12 Claims, 4 Drawing Sheets

(51) Int. Cl.
*A61B 5/0488* (2006.01)
*A61B 5/11* (2006.01)
*A61F 2/70* (2006.01)

(52) U.S. Cl.
CPC .............. *A61B 5/1126* (2013.01); *A61F 2/60* (2013.01); *A61F 2002/704* (2013.01)

(56) References Cited

U.S. PATENT DOCUMENTS

| | | |
|---|---|---|
| 8,626,472 B2 | 1/2014 | Solinsky |
| 2002/0052663 A1 | 5/2002 | Herr |
| 2003/0185450 A1 | 10/2003 | Garakani |
| 2004/0032796 A1 | 2/2004 | Chu |
| 2005/0033146 A1 | 2/2005 | Troyansky |
| 2006/0015470 A1 | 1/2006 | Lauer |
| 2006/0155386 A1 | 7/2006 | Wells |
| 2007/0129622 A1 | 6/2007 | Bourget |
| 2009/0030530 A1 | 1/2009 | Martin |
| 2009/0319054 A1 | 12/2009 | Sankai |
| 2012/0004736 A1 | 1/2012 | Goldfarb |
| 2012/0083901 A1 | 4/2012 | Langlois |
| 2012/0101596 A1 | 4/2012 | Dietl |
| 2014/0031711 A1* | 1/2014 | Low .................. A61B 5/16 600/544 |

OTHER PUBLICATIONS

Pribil et al. "Determination of Formant Features in Czech and Slovak for GMM Emotional Speech Classifier," Radioengineering, vol. 22, No. 1, Apr. 2013.

Freye et al. "Cerebral monitoring in the operating room and the intensive care unit," Journal of Clinical Monitoring and Computing (2005) 19: 1-76.

Kugler et al., "Mobile EMG Aralysis with Applications in Sport and Medicine," Proceedings of the 1st Biomedcal Signal Analysis (Rio de Janeiro, Oct. 21-24, 2013).

Phinyomark et al., "A Novel Feature Extraction for Robust EMG Pattern Recognition," Journal of Computing, vol. 1, Issue 1, Dec. 2009.

Farrell et al., "A method to determine the optimal features for control of a powered lower-limb prostheses," Proc. 33rd Annual Int'l Conf. IEEE Engineering in Medicine and Biology Soc., (2011) pp. 6041-6046.

Subasi, "Classification of EMG signals using combined features and soft computing techniques," Applied Soft Computing 12 (2012) 2188-2198.

Oskoei et al., "Myoelectric control systems—A survey," Biomedical Signal Processing and Control 2 (2007) 275-294.

Englehart et al., "Classification of the myoelectric signal using time-frequency based representations," Medical Engineering & Physics 21 (1999) 431-438.

* cited by examiner

POWERED PROSTHETIC DEVICES USING EMG-BASED LOCOMOTION STATE CLASSIFIER

CROSS-REFERENCE TO RELATED APPLICATIONS

This application is a 371 of PCT/US2014/045608 filed on Jul. 7, 2014. PCT/US2014/045608 claims the benefit of US Provisional Application 61/845905 filed on Jul. 12, 2013.

STATEMENT OF GOVERNMENT SPONSORED SUPPORT

This invention was made with Government support under contract no. W81XWH-09-2-0144 awarded by the Department of Defense. The Government has certain rights in the invention.

FIELD OF THE INVENTION

The present invention relates generally to the field of prosthetics. More specifically, it relates to improved control techniques for powered prosthetic devices.

BACKGROUND OF THE INVENTION

To restore the locomotion capabilities of lower limb amputees many prosthetic legs have been developed. Most of the commercially available lower limb prostheses are either passive or powered devices controlled with finite-state machine (FSM) approaches. Current control strategies within the FSM approach do not allow amputees a seamless and natural transition between locomotion modes. Therefore, there is a need for a strategy which can predict the intended locomotion task and transition ahead of time to achieve the desired damping, allowing safe and smooth locomotion transitions.

SUMMARY OF THE INVENTION

In one aspect, the invention provides a method for real-time detection of transitions between locomotion modes or states using muscle activation signals as input. The method relates to myoelectric control, electromyography (EMG) classification, locomotion state detection, and transition detection. While the primary application is to powered prosthetic devices, the techniques have general application to any device that uses a locomotion state controller.

Embodiments of the invention feature use of higher order moments of a spectrogram-induced histogram derived from muscle activation signals to distinguish between signal patterns associated with transition phases between locomotion modes (i.e., level walking, stair ascent/descent, ramp ascent/descent). In addition, embodiments provide accurate classification of transitions between locomotion states within 10 ms. Embodiments also provide algorithms specifically suited to implementation in microprocessor code for integration with existing powered prosthetic/orthotic control platforms. Further, these embodiments allow more user-friendly application of the powered prosthetic devices, as the simple if-else rules provide more intuitive tuning of the device by a clinician or technician.

An advantage of this approach is that it allows determination of transition between locomotion states (e.g., level walking to stair descent) in as little as 10 ms. Previous approaches have used offline determination of locomotion state changes, requiring users of powered locomotion devices (prostheses and orthoses) to stop and trigger state transitions with non-locomotive signal inputs (e.g., external triggering, co-contraction of muscles, etc.). The previous offline approaches require non-functional halts to locomotion in the variable terrains encountered every day.

A significant new feature of embodiments of the invention is the utilization of features such as $3^{rd}$ and $4^{th}$ order moments (skewness and kurtosis) of a spectrogram-induced histogram derived from muscle activation signals to distinguish between signal patterns associated with transition phases between locomotion modes (e.g., level walking, stair ascent/descent, ramp ascent/descent). Benefits include real-time control of transitions between locomotion states, and the utilization of this enhanced control using a simple machine code within commonly used microprocessors. Commercial use of the techniques of the present invention include incorporation of the technique into already existing powered prosthetic/orthotic control platforms, allowing existing systems to achieve smooth transitions between locomotion states.

We present a time-frequency derived histogram model for classification. This approach is simple, elegant, and less computationally complex. We further present a novel prior knowledge approach to be integrated with the classifier.

In one aspect, the invention provides a method for real-time control of a prosthetic device using EMG-based locomotion state classification. The method includes sampling surface EMG signals from muscles to produce EMG data, computing a histogram of a time-frequency spectrogram of the EMG data, computing matching scores between the histogram of the time-frequency spectrogram of the EMG data and stored histograms for locomotion steady states and locomotion transition states, classifying using if-else rules and the matching scores the histogram as representing a locomotion steady state or locomotion transition state in the prosthetic device, and controlling the prosthetic device using the computed transitions between locomotion modes.

Alternatively, instead of computing matching scores between the histograms, the method may include computing a feature value, such as skewness or kurtosis, of the histogram of the time-frequency spectrogram of the EMG data, comparing the feature value with stored feature values for locomotion steady states and locomotion transition states. In this case, the classifying is based on the feature value instead of the matching scores.

In one embodiment, the time-frequency spectrogram of the EMG data is a 2D spectrogram, and the time-frequency spectrogram of the EMG data comprises energy values assigned to a grid of time bins and frequency bins for EMG data in a time window. The energy values may be quantized values corresponding to fractions of a maximum energy. For example, the quantized values may be binary values where a value of 1 represents an energy exceeding a predetermined threshold energy and a value of 0 represents an energy not exceeding the predetermined threshold energy. In one embodiment, the histogram comprises a number of occurrences of maximum energy for frequency bins in the time-frequency spectrogram.

The classifying preferably is performed using hierarchical if-else fuzzy classification rules. For example, the classifying may include a main classification between locomotion transition state and locomotion steady state, and a subclassification between locomotion transition states and locomotion steady states. In some embodiments, the classifying further includes using a prior locomotion state and a state diagram specifying constraints on locomotion states accessible from other locomotion states. The locomotion steady states preferably include level walking, stair ascent/descent, and ramp ascent/descent, and the locomotion transition states preferably include transitions between the locomotion steady states.

DETAILED DESCRIPTION

Figure 1:
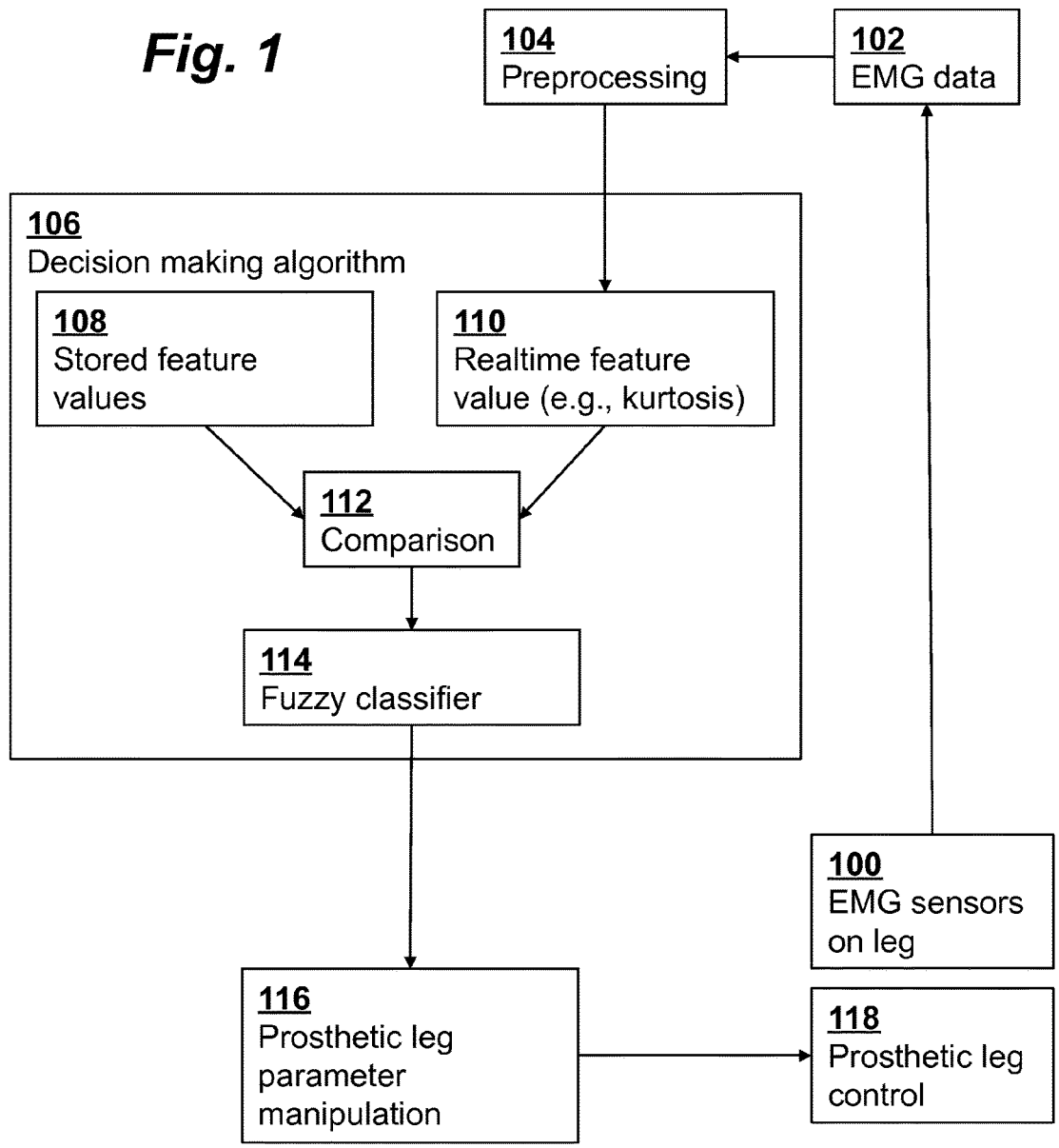
FIG. 1 is a functional block diagram illustrating components and associated functions according to an embodiment of the invention.

FIG. 1 is a functional block diagram illustrating components and associated functions according to an embodiment of the invention. EMG sensors 100 attached to a leg provide signals which are sampled by a data processor to produce EMG data 102. A microprocessor performs preprocessing 104 of the EMG data, and the resulting preprocessed data is provided to a decision making algorithm 106 implemented by a microprocessor. More specifically, the microprocessor calculates a real time feature value (e.g., kurtosis) 110 which is compared 112 with a stored feature 108 retrieved from a computer memory. The results of the comparison are provided to a fuzzy classifier 114 which determines a locomotion steady state or transition. A prosthetic leg control circuit then uses the locomotion steady state or transition information for prosthetic leg parameter manipulation 116 that is used to actuate mechanical prosthetic leg control 118. Embodiments of the invention primarily relate to features of the preprocessing 104 and decision making algorithm 106. In a commercial device according to an embodiment of the present invention, these steps may be implemented in a microprocessor, such as those already existing in the current state-of-the-art powered devices. These will be described in more detail in relation to FIG. 2.

Figure 2:
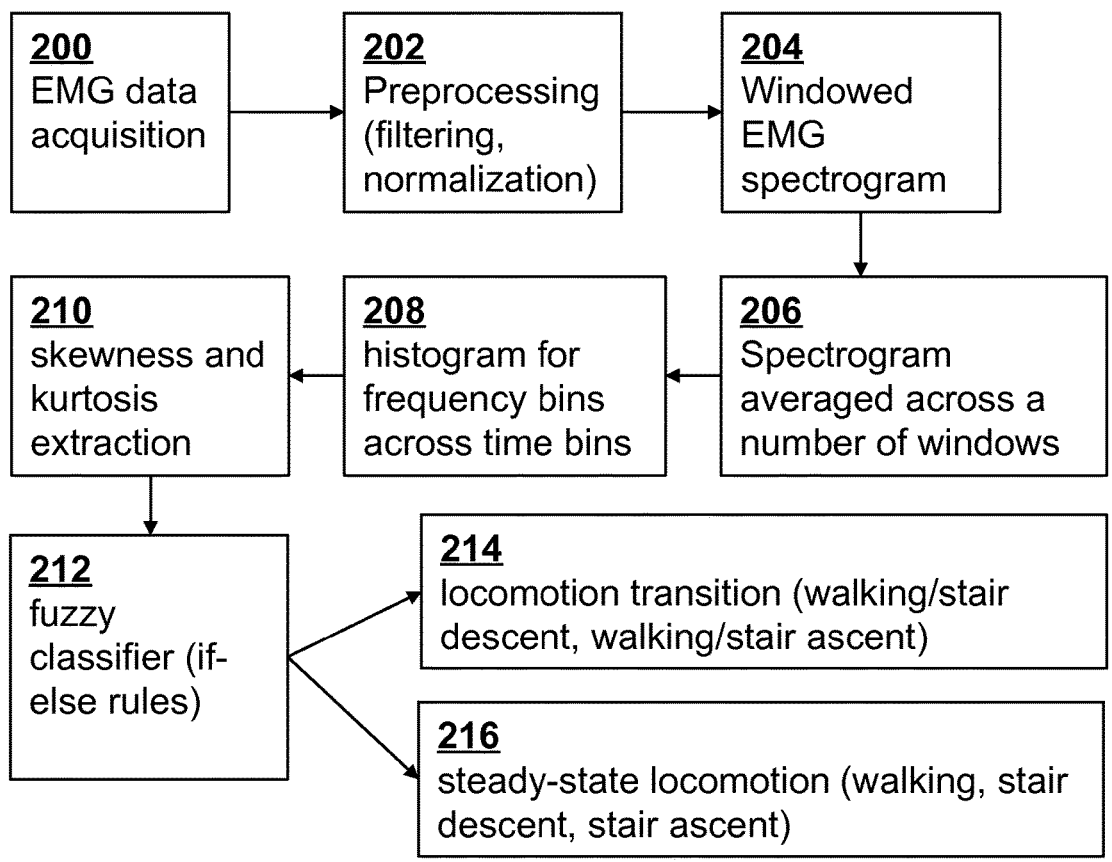
FIG. 2 is a functional block diagram illustrating main steps in a method for real-time control of a prosthetic device using EMG-based locomotion state classification according to an embodiment of the invention.

FIG. 2 is a functional block diagram illustrating main steps in a method for real-time control of a prosthetic device using EMG-based locomotion state classification according to an embodiment of the invention. Data from EMG sensors is sampled in data acquisition step 200 and then filtered and normalized in preprocessing step 202. The preprocessed data is then used to create windowed EMG spectrogram in step 204, and the spectrogram is averaged across multiple windows in step 206. In step 208 a histogram for frequency bins across time bins is created from the spectrogram. One or more features (e.g., skewness and kurtosis) are then extracted from the histogram in step 210. The extracted feature is then processed in a fuzzy classifier 212 using if-else rules to determine whether the EMG data are representative of a locomotion transition 214 or a locomotion steady-state 216. These steps are described below in more detail.

Surface EMG data may be recorded from leg muscles using passive surface electrodes (Ag/Ag—Cl) placed in bipolar single differentiation configuration on the tibialis anterior (TA), gastrocnemius medialis (GM), rectus femoris (RF), vastus lateralis (VL), biceps femoris (BF), gluteus maximus (Gmax), and/or gluteus medius (Gmed) of both legs. Local transmitters may be placed near to the collection sites, either embedded into the prosthetic device structure, or external to the device.

EMG data are preferably sampled at 1500 Hz and bandpass filtered between 3 and 500 Hz, using standard techniques. The sampled EMG data is then processed to perform magnitude normalization.

A spectrogram for each 256 ms data segment is generated with 64 ms of sliding window and 50% overlap. For example, a periodogram approach may be used to calculate the spectral density $P_x$ of the data segment as $$P_x(m, \omega) = 1/N \, \Sigma_{n=0, N-1} \, x(n) * W(n-m) * \exp(-j\omega n)$$

where x(n) is the normalized EMG magnitude for data point n, N is the total number of data points in the data segment, $\omega$ is the frequency and m is the length of rectangular window, W. The values of the spectrogram may then be calculated as the magnitude square of each periodogram as $$\text{Spectrogram } \{x(n)\}(m, \omega) = |P_x(m, \omega)|^2$$

The periodogram gives a good estimate of spectral density of non-stationary signals like EMG or electroencephalography, calculating the Fourier transform of autocorrelation from the signal to give a better estimate of non-stationary signals.

The window size m may be empirically determined based on principles of the present invention. The value of m should be decided based on the tradeoff between accuracy and response time. A longer window size will give good accuracy but at the cost of slow response of the prosthetic device. Hence, the value of m must be decided empirically based on acceptable accuracy. Initial results show 64 ms to be a favorable value for m.

The spectrogram may be generated using other techniques as well. For example, the short time Fourier transform of the EMG data may be computed to obtain the energy values for the spectrogram.

In some embodiments the spectrogram may be compressed using threshold based binary conversion (TBBC). Each frequency bin in the spectrogram may be assigned a binary value based on its energy level with respect to maximum energy level in the spectrogram using a predetermined threshold value. For example, any frequency bin having value equal to or greater than 50% of maximum energy level in the spectrogram is assigned value 1; else 0. The predetermined threshold may be empirically determined. A high threshold value of 90%, for example, may result in the omission of critical information from the spectrogram while a low value of 10% may include unwanted noisy and redundant information.

Figure 3A:
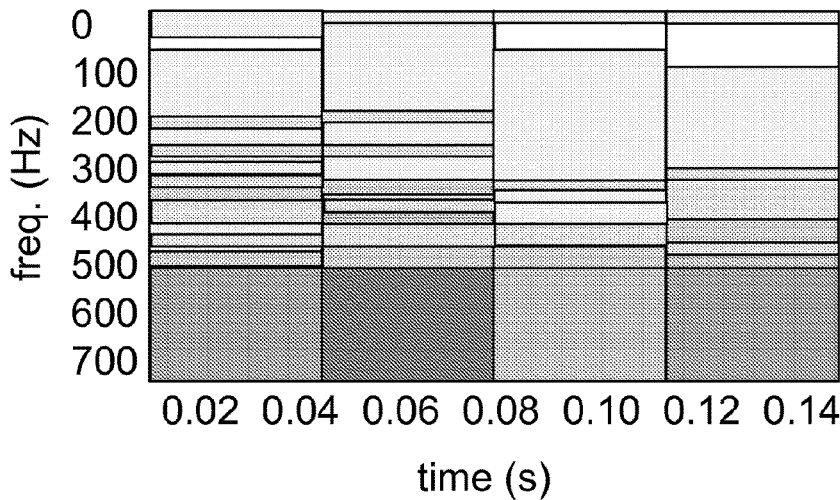
FIG. 3A illustrates a time-frequency spectrogram according to an embodiment of the invention.

Alternative embodiments may assign the weighted proportional value for the bins based on how close or near the bin's energy level is to the maximum energy level. For example, a frequency bin with 80% of maximum energy level may be assigned a value of 8, and the frequency bin with 70% of maximum energy level may be assigned a value of 7. This approach could be further focused to the 1% resolution level. More generally, each frequency bin may be quantized by assigning it an integer according to its fraction of the maximum energy level, e.g., selecting an integer from 0 to M−1 corresponding to fractions in the ranges of 0 to 1/M, 1/M to 2/M, . . . , M−1/M to 1. Larger values of M provide a smoother histogram and may improve the classification accuracy at the cost of less data compression. FIG. 3A illustrates a spectrogram according to an embodiment of the invention. The spectrogram is represented graphically as rectangular frequency and time bins in a frequency vs. time plot, where the shading of each rectangle represents the quantized energy level for that frequency-time bin. The example spectrogram in FIG. 3A is generated from EMG data of tibialis anterior (TA) muscle during a transition from Level Ground (LG) to Stair Descent (SD).

The binary converted spectrograms are summed by bin and divided by the number of windows to calculate average spectrogram.

The spectrogram values are accumulated across the time bins to develop a histogram. This may be viewed as a conversion of a 2-D spectrogram into a 1-D histogram, where the bars of the histogram represent the weighted occurrence of energy distribution of EMG signal in the spectrogram for corresponding time bins. In this way, the 1-D histogram efficiently restores the critical information (towards the classification of locomotive task) of the spectrogram and at the same time compresses the feature space of the spectrogram, which is critical for real time implementation. As used herein, a spectrogram is a time-frequency energy distribution of a signal. It supports narrow "high" frequency signals with fixed time-frequency resolution.

The conversion of a quantized 2-D spectrogram to a 1-D histogram is a binary conversion. In other embodiments, a fuzzy conversion may be used to make the algorithms more efficient for real time implementation. This provides a simple threshold-based classifier for classification between locomotive tasks.

Figure 3B:
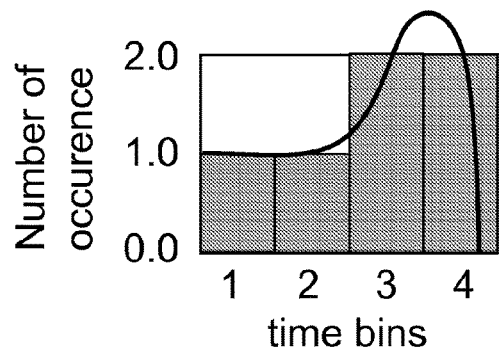
FIG. 3B shows an example of a histogram for time bins in the spectrogram of FIG. 3A according to an embodiment of the invention.
Figure 3C:
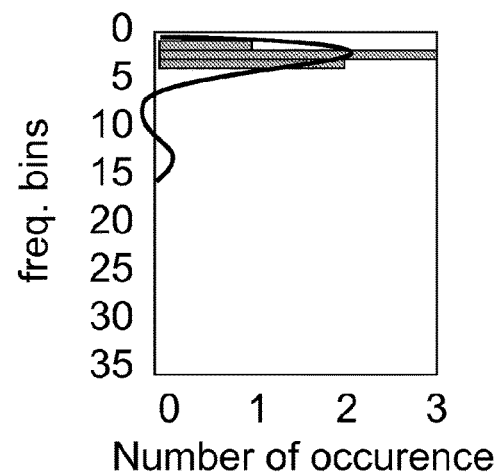
FIG. 3C shows an example of a histogram for frequency bins in the spectrogram of FIG. 3A, according to an embodiment of the invention.

In some embodiments, the histogram corresponds to the frequency bins having maximum energy, and may be computed for any of various window sizes, such as 6.25% (0.01 secs), 12.5% (0.02 secs), 25% (0.04 secs) and 50% (0.18 secs) of the data segment. FIG. 3B shows an example of a histogram for time bins in the spectrogram of FIG. 3A, where each bin represents 0.04 s. Alternatively, a histogram may correspond to frequency bins, as shown in FIG. 3C, where each bin represents 23.74 Hz.

Feature values (or scores) of the histograms are extracted for use in classification. For example, the 3rd and 4th order moments of histogram, skewness and kurtosis respectively, may be used to represent the histograms and serve as expanded feature space for classification of transition between locomotion states. For example, in one instance, the kurtosis for a histogram of Tibialis Anterior was observed to be 6.14 and 3.13, respectively for stair descent and stair ascent. This provides a reasonable separation between classes for a reliable classifier. Addition of more muscles may improve the separation margin for better classification accuracy at the cost of more sensors leading to higher dimensional space. The fourth order moment of histogram, kurtosis, may be used alone as a feature for the classification of locomotion transition. Some embodiments, however, may also include the skewness of histogram as an additional feature value. Other embodiments may include other scores or features calculated from the histograms.

The first step in classification is comparing a feature value K computed in real time from recent EMG data to stored feature values $K_i$. For example, in one embodiment, the kurtosis value obtained in real time is compared to the stored value inside the microprocessor and fed to a fuzzy classifier for classification.

The stored feature values are determined during a calibration or training phase. For example, during this phase, a user of the device is instructed to complete a series of successful level-ground to stair ascent transition trials. Each trial is constructed so the user has at least three gait cycles pre- and post-transition. The users are instructed to walk at a natural self-selected pace throughout the trial. The feature value from each muscle for steady state and locomotion transition is computed and stored inside the microprocessor, together with the associated known steady state or locomotion transition.

The classifier algorithm is based on hierarchical if-else fuzzy rules. This allows more robust real time control for integration into existing control platforms prosthesis design. According to one embodiment, the classifier uses a two-stage hierarchical classification scheme. First, the classifier classifies the EMG data for a main class, to distinguish between transitional event and steady state event. Second, the classifier further classifies the class into subclasses. In particular, the transitional event is classified into subclasses, Ground level (GL) to Stair Ascent (SA) or Ground level (GL) to Stair Descent (SD). Similarly, the steady state event is classified as subclasses GL, SA or SD.

Figure 4A:
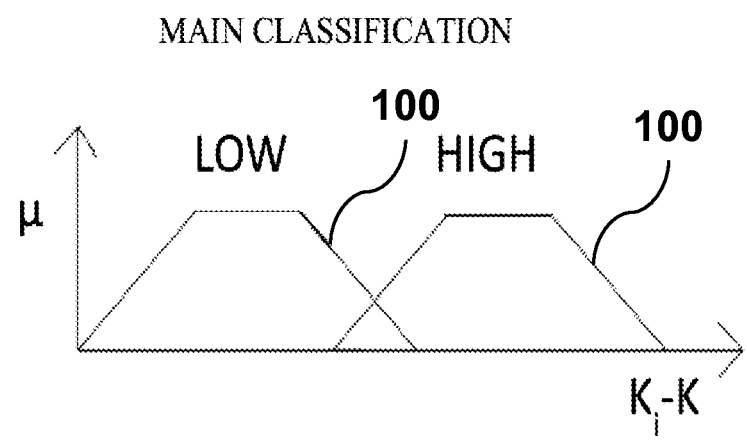
FIG. 4A is a graph of a classifier function for a main classification step according to an embodiment of the invention.
Figure 4B:
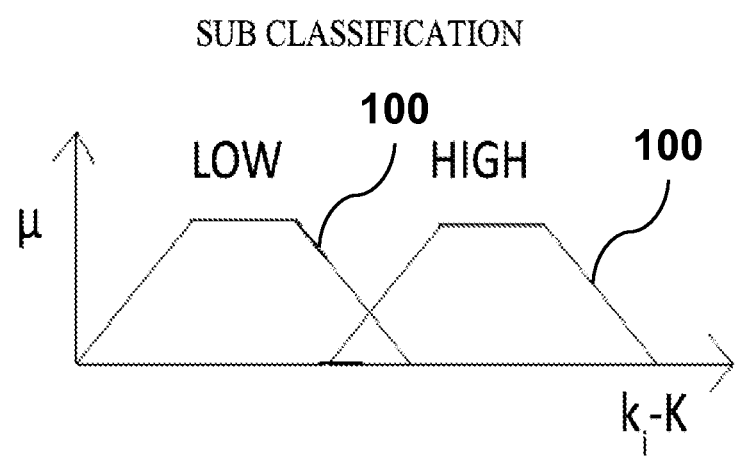
FIG. 4B is a graph of a classifier function for a sub-classification step according to an embodiment of the invention.

FIGS. 4A and 4B are graphs of fuzzy classifier functions used for the main classification and subclassification of the classifier, respectively. First, as shown in FIG. 4A, the difference between the real time feature value K and each stored feature value $K_i$ for the main classes is used to evaluate the fuzzy classifier function to distinguish between main classes. The if-else rules are as follows:

If $(K_1-K)$ is LOW and $(K_2-K)$ is HIGH, then select class $C_1$.

If $(K_1-K)$ is HIGH and $(K_2-K)$ is LOW, then select class $C_2$.

In these expressions, LOW and HIGH represent the linguistic variable with membership value μ, $K_1$ is the feature value for locomotion transition state $C_1$, and $K_2$ is the feature value for locomotion steady state $C_2$.

Second, as shown in FIG. 4B, the difference between the real time feature value K and each stored feature value $k_i$ for the subclasses is used to evaluate the fuzzy classifier function to distinguish between subclasses. There are two cases, depending on the result of the main classification.

Case 1. For locomotion transition state $C_1$, the if-else rules are as follows:

If $(k_1-K)$ is LOW and $(k_2-K)$ is HIGH, then select class $c_1$ (GL to SD).

If $(k_1-K)$ is HIGH and $(k_2-K)$ is LOW, then select class $c_2$ (GL to SA).

For other transitions we will have similar k terms from training data which are stored in the microprocessor. For example $k_6$ for GL to RA (Ramp Ascent). Accordingly, the rules can be designed to facilitate the additional k terms. Here we show an example for SA and SD as representative transitions. The number of rules will increase as the number of transition types increase.

Case 2. For locomotion steady state $C_2$, the if-else rules are as follows:

If $(k_3-K)$ is LOW and $(k_4-K)$ is HIGH and $(k_5-K)$ is HIGH, then select class $c_3$ (GL).

If $(k_3-K)$ is HIGH and $(k_4-K)$ is LOW and $(k_5-K)$ is HIGH, then select class $c_4$ (SA).

If $(k_3-K)$ is HIGH and $(k_4-K)$ is HIGH and $(k_5-K)$ is LOW, then select class $c_5$ (SD).

The weighting strength for each rule is defined by F(Rule)= $\mu$(LOW)*$\mu$(HIGH).

In effect, the two-step classification helps increase computational efficiency of the classification.

In another embodiment, classification may be performed using matching scores (MS) and then discriminating functions in the form of if-else rules. For example, if $S_k$ is the stored histogram for class k where k is W, W to SA, or SA, then for real time data spectrogram, T, the matching score $MS_k$ for a class k may be defined as follows:

$$MS_k = \Sigma_{m=1,7} \Sigma_{i=1,M} \Sigma_{j=1,N} S_{k(i,j,m)} * T_{i,j,m}$$

where i and j are the time and frequency bin index, respectively, and m is the index for muscles. For reduced neural information m can vary in the above equation. The classification rule decides class k with highest matching score as follows:

If $MS_W > MS_{W-SA}$ and $M_{SW} > MS_{SA}$, then class is W
If $MS_{W-SA} > M_{SW}$ and $MS_{W-SA} > MS_{SA}$, then class is W-SA
If $MS_{SA} > MS_{W-SA}$ and $MS_{SA} > MS_{W-SA}$, then class is SA.

As discussed above, one embodiment utilizes the numeric weighted value for each frequency bin assigned based on its energy level with respect to maximum energy level in the spectrogram. Using a Fuzzy Weighted Conversion scheme, a membership value is assigned within a certain linguistic variable, to each frequency bin rather than a numeric value. This embodiment skips the fuzzification step used by previous schemes of threshold/weighted binary conversion and hence will reduce the computational time.

In some embodiments, the hierarchical classifier may include stages of terrain type classification, ramp/stair classification, and ascent/descent classification.

In some embodiments, overall transition classification accuracy was highest in 333 ms window size. In other embodiments, a 250 ms window size may be used.

In some embodiments, prior knowledge of classification is used to improve current classification when combined with a state diagram constraining the allowed states accessible from a given state. This prior knowledge may be integrated into the technique as follows: If the previous class is W (walk) then there is no possibility that the next class can be SA (stair ascent). The only possibility for next class can be W or W-SA (transition from W to SA). It cannot be a SA because for SA to be a possible class the prior gait cycle must be either W-SA or SA. Hence, for a given EMG data set with prior knowledge W, the classification should not be computed for SA. Thus, prior knowledge is able to restrict the possible intended locomotion state, and effectively reduce computation time and increase classification accuracy. Thus, for a given set of EMG data the use of prior knowledge effectively reduces the class space.

In a variety of test cases, using prior knowledge substantially increased classification accuracy in all data segments. To implement the prior knowledge integration scheme the only requirement is to store the previous locomotion mode for recall during classification. This storage of prior knowledge can be done using some bits in the memory depending on the number of locomotion modes considered. For example, if there are three locomotion modes, say W, W-SA and SA, we only need 2 bits for storage (i.e., $\log_2 n$) where n is the sum of number of locomotion modes and transitions. This storage requirement is then quite minimal.

Embodiments described herein focus on an example using EMG data from one of the muscle activation data sets. Specifically, the technique has been illustrated with data from the tibialis anterior from one limb. However, muscle activation data from additional muscles per leg may be collected in the same data collection sessions and processed in accordance with the principles of the invention to increase the sensitivity of the locomotion transition classifier.

Preferably, data from TA and/or MG muscles are used, as they produce EMG data with the highest discriminating power in classifying all locomotion modes, and consistent in all data segments. In some embodiments, the criterion of Euclidean distance between histograms of different classes may be used to observe the discriminating power of muscles. Using this metric helps select the few muscles that are most rich in classification information and thus determine which muscles should be given priority while developing training protocols to allow amputees to have more neural control of the powered prosthesis. Based on the individual characteristics of a residual limb and the performance of the residual muscles in discriminating classes, it is more likely that a customized prosthesis controller may be implemented.

To understand the set of muscles that best discriminates the classes of W, SA, and W-SA we calculated the Euclidean distance between histograms of a pair of classes in each window for each muscle, which is less computationally complex than other iterative algorithms. Specifically, if $P_i$ and $Q_i$ are the histogram values of the $i^{th}$ bin for two different classes and d is the total number of bins, then these histogram values may be viewed as coordinates defining two points in a d-dimensional Euclidean space. The Euclidean distance $D_{euc}$ may then be calculated in the conventional way. Further, for each window, the muscle with highest $D_{euc}$ may be deemed to be the priority muscle. Similarly, secondary or associated/assistant muscles may be selected. This approach effectively reduces the neural control information needed for classification, which is an important design goal for neural controlled prostheses.

The invention claimed is:

1. A method for real-time control of a prosthetic device using EMG-based locomotion state classification, the method comprising:
    sampling surface EMG signals from muscles to produce EMG data;
    computing a histogram of a time-frequency spectrogram of the EMG data;
    computing a feature value of the histogram of the time-frequency spectrogram of the EMG data;
    comparing the feature value with stored feature values for locomotion steady states and locomotion transition states;
    classifying using if-else rules the feature value as representing a locomotion steady state or locomotion transition state in the prosthetic device;
    controlling the prosthetic device using the computed transitions between locomotion modes.

2. The method of claim 1 wherein the time-frequency spectrogram of the EMG data is a 2D spectrogram.

3. The method of claim 1 wherein the feature value is skewness or kurtosis.

4. The method of claim 1 wherein the time-frequency spectrogram of the EMG data comprises energy values assigned to a grid of time bins and frequency bins for EMG data in a time window.

5. The method of claim 4 wherein the energy values are quantized values corresponding to fractions of a maximum energy.

6. The method of claim 5 wherein the energy values are binary values where a value of 1 represents an energy exceeding a predetermined threshold energy and a value of 0 represents an energy not exceeding the predetermined threshold energy.

7. The method of claim 1 wherein the histogram comprises a number of occurrences of maximum energy for frequency bins in the time-frequency spectrogram.

8. The method of claim 1 wherein classifying comprises hierarchical if-else fuzzy classification rules.

9. The method of claim 8 wherein classifying comprises a main classification between locomotion transition state and locomotion steady state, and a subclassification between locomotion transition states and locomotion steady states.

10. The method of claim 1 wherein classifying comprises using a prior locomotion state and a state diagram specifying constraints on locomotion states accessible from other locomotion states.

11. The method of claim 1 wherein the locomotion steady states comprise level walking, stair ascent/descent, and ramp ascent/descent, and wherein the locomotion transition states comprise transitions between the locomotion steady states.

12. A method for real-time control of a prosthetic device using EMG-based locomotion state classification, the method comprising:
- sampling surface EMG signals from muscles to produce EMG data;
- computing a histogram of a time-frequency spectrogram of the EMG data;
- computing matching scores between the histogram of the time-frequency spectrogram of the EMG data and stored histograms for locomotion steady states and locomotion transition states;
- classifying using if-else rules and the matching scores the histogram as representing a locomotion steady state or locomotion transition state in the prosthetic device;
- controlling the prosthetic device using the computed transitions between locomotion modes.

* * * * *